United States Patent [19]

Katoh et al.

[11] Patent Number: 4,868,178
[45] Date of Patent: Sep. 19, 1989

[54] PYRIDINYL-S-TRIAZINE DERIVATIVES

[75] Inventors: Tsuguhiro Katoh, Osaka; Kiyoto Maeda; Masao Shiroshita, both of Hyogo; Norihisa Yamashita, Osaka; Yuzuru Sanamitsu; Satoru Inoue, both of Hyogo, all of Japan

[73] Assignee: Sumitomo Chemical Company, Ltd., Osaka, Japan

[21] Appl. No.: 153,680

[22] Filed: Feb. 8, 1988

[30] Foreign Application Priority Data

Feb. 13, 1987 [JP] Japan .................................. 62-32240
Feb. 13, 1987 [JP] Japan .................................. 62-32241

[51] Int. Cl.$^4$ ..................... A01N 43/66; C07D 401/04
[52] U.S. Cl. .................................... 514/241; 544/216; 544/180
[58] Field of Search ................. 544/180, 216; 514/241

[56] References Cited

PUBLICATIONS

Schaefer, "Synthesis of the s-Triazine System . . . Imidates", J. Org. Chem., 27, pp. 3608-3613 (Oct. 1962).
W. Fife, "Regioselective Cyanation of Pyridine . . . Reaction", J. Org. Chem., 48, pp. 1375-1377, (1983).
Y. Honma et al., "Antiallergic Agents . . . pyridinecarboxamides", J. Med. Chem., 26, pp. 1499-1504, (1983).
Fife, "Cyanation in the Pyridine Series . . . Reactions", Heterocycles, vol. 22, No. 10, 1984.

Primary Examiner—John M. Ford
Attorney, Agent, or Firm—Sughrue, Mion, Zinn, Macpeak & Seas

[57] ABSTRACT

A novel pyridinyl-s-triazine derivative of the formula below, a method for preparation thereof and a fungicide containing it,

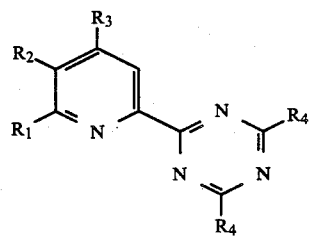

which is effective as fungicide.

7 Claims, No Drawings

PYRIDINYL-S-TRIAZINE DERIVATIVES

This invention relates to a novel pyridinyl-s-triazine derivative, a method for preparation thereof and a fungicide containing it as an active ingredient.

The pyridinyl-s-triazine derivatives such as 2,4-dimethyl-6-(2-pyridinyl)-s-triazine (J. Org. Chem., 27, 3608-3613 (1962)) are known.

However, it is not known that the pyridinyl-s-triazine derivatives have fungicidal effect at all.

An object of the present invention is to provide a compound having preventive and curative controlling effects against many plant diseases.

The present inventors have found that pyridinyl-s-triazine derivatives having the formula (I) mentioned below or their salts (hereinafter referred simply to as the present compound) have excellent fungicidal activity:

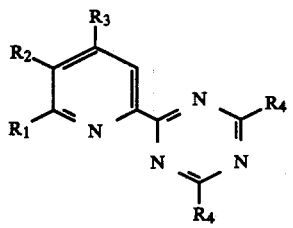

wherein $R_1$ is a $C_1$-$C_7$ alkyl group; or a phenyl group optionally substituted with at least one member selected from the group consisting of halogen, $C_1$-$C_3$ alkyl, $C_1$-$C_3$ alkoxy and $C_1$-$C_3$ haloalkyl; $R_2$ and $R_3$ which may be the same or different are a hydrogen atom or a $C_1$-$C_3$ alkyl group, or $R_1$-$R_2$ are, taken together, a polymethylene group of the formula: $+CH_2+_n$ in which n is 3 or 4 and $R_4$ is a $C_1$-$C_4$ alkyl group, with the proviso that when $R_1$ is methyl or ethyl group, $R_4$ is not methyl group. Preferably, $R_1$ is a $C_3$-$C_5$ alkyl group, or a phenyl group optionally substituted with at least one member selected from the group consisting of halogen, methyl, ethyl, methoxy, ethoxy and trifluoromethyl group; $R_2$ and $R_3$ which may be the same or different are a hydrogen atom or a methyl group and $R_4$ is a $C_1$-$C_3$ alkyl group.

More preferably, $R_1$ is a $C_3$-$C_5$ alkyl group, or a phenyl group optionally substituted with at least one member selected from the group consisting of halogen, methyl and trifluoromethyl group; $R_2$ and $R_3$ which may be the same or different are a hydrogen atom or methyl group and $R_4$ is a $C_1$-$C_3$ alkyl group.

Plant diseases that can be controlled by the present compound include the following:
Rice: *Pyricularia oryzae*, *Cochliobolus miyabeanus* and *Rhizoctonia solani*;
Barley and wheat: *Erysiphe graminis f. sp. hordei*, *E. graminis f. sp. tritici*, *Pyrenophora graminea*, *Puccinia striiformis*, *P. graminis*, *P. recondita*, *P. hordei*, *Pseudocercosporella herpotrichoides*, *Rhynchosporium secalis*, *Septoria tritici* and *Leptosphaeria nodorum*;
Citrus: *Diaporthe citri* and *Elsinoe fawcetti*;
Apple: *Podosphaera leucotricha*, *Alternaria mali* and *Venturia inaequalis*;
Pear: *Venturia nashicola* and *Alternaria kikuchiana*;
Peach: *Sclerotinia cinerea*;
Grape: *Elsinoe ampelina*, *Glomerella cingulata* and *Uncinula necator*;
Melon crops: *Colletotrichum langenarium* and *Sphaerotheca fuliginea*;
Tomato: *Alternaria solani* and *Phytophthora infestans*;
Eggplant: *Phomopsis vexans*;
Rape: *Alternaria japonica* and *Cercosporella brassicae*;
Welsh onion: *Puccinia allii*;
Soybean: *Cercospora kikuchii* and *Elsinoe glycines*;
Kidney bean: *Colletotrichum lindemuthianum*;
Peanut: *Mycosphaerella personatum* and *Cercospora arachidicola*;
Pea: *Erysiphe pisi*;
Potato: *Alternaria solani*;
Sugar beet: *Cercospora beticola*;
Rose: *Diplocarpon rosae* and *Sphaerotheca pannosa*;
Crop plants:
*Botrytis cinerea* and *Sclerotinia sclerotiorum*.
Diseases more controllable among the above are
Rice: *Pyricularia oryzae*,
Barley and wheat: *Septoria tritici*, *Pseudocercosporella herpotrichoides*, and most controllable is
*Pyricularia oryzae* against rice.

The pyridinyl-s-triazine derivative (I) can be typically prepared by the methods as shown below:

The present compound can be obtained by reacting a salt of picoline amidine derivative of the formula:

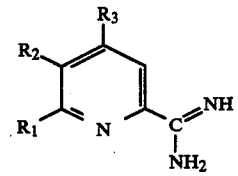

wherein $R_1$, $R_2$ and $R_3$ are each defined as above, with imidate derivative of the formula:

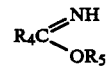

wherein $R_4$ is defined as above and $R_5$ is a lower alkyl group.

Examples of the salt of picoline amidine derivative are hydrochloride, hydrobromide, acetate and formate.

The reaction is usually carried out in the absence of solvent.

The reaction may be carried out at about 10° to about 100° for about 10 minutes to about 48 hours.

The imidate derivative (III) may be used in amounts of about 3 equivalents to 1 equivalent of the salt of picoline amidine derivative (II).

After the reaction, the reaction mixture is concentrated in vacuo to give a residue. Then, the residue is subjected to usual post-treatment such as extraction with organic solvent, concentration and, if necessary, chromatography to obtain the objective compound (I).

The present compound having the formula (I) is easily able to convert to salts thereof by reacting the compound with strong acid such as hydrochloric acid, hydrobromic acid, sulfuric acid or nitric acid.

The salt can be typically obtained by the procedures shown below. The compound of the formula (I) is dissolved in a solvent and then about one equivalent of the acid in the form of gas or aqueous solution is added thereto under ice cooling or at room temperature. After being left to stand for about 10 minutes to about one hour, the solution is subjected to post-treatment such as concentration under reduced pressure, and if necessary recrystallization. Examples of the solvent are lower alcohol such as methanol, ethanol, etc.; aromatic hydrocarbon such as toluene, benzene, etc.; ether such as ethyl ether, tetrahydrofuran, dioxane, etc.; halogenated hydrocarbon such as chloroform, etc.; ketone such as acetone, etc.; ester such as ethyl acetate, etc.; hydrocarbon such as hexane, etc.; water or a mixture thereof.

Salt of picoline amidine derivative of the formula (II) is typically prepared by the following reaction scheme:

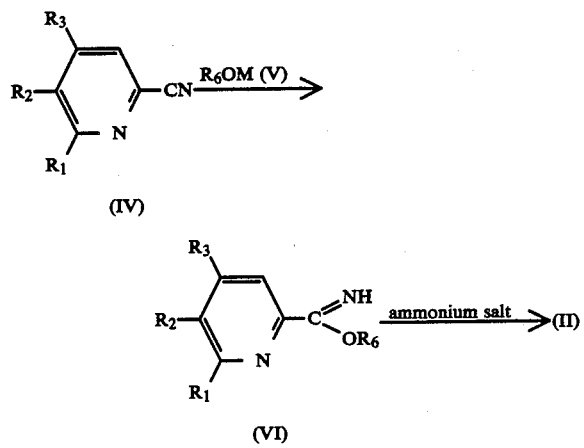

wherein $R_1$, $R_2$ and $R_3$ are defined as above, $R_6$ is a lower alkyl group and M is an alkali metal atom.

An imidate derivative of the formula (VI) is prepared by reacting a cyanopyridine derivative of the formula (IV), which is prepared by a method described in J. Org. Chem., 48, 1375-1377 (1983) or J. Med. Chem., 26, 1499-1504 (1983), with an alkoxide of the formula (V).

The salt of picoline amidine derivative of the formula (II) is prepared by reacting the imidate derivative of the formula (VI) with an ammonium salt.

Details of the above production are as follows.

A reaction between the compound of the formula (IV) and the compound of the formula (V):

Examples of alkali metal atom in the alkoxide (V) are a sodium atom, a potassium atom, etc. The reaction is usually carried out in the presence of a solvent at about 10° to about 50° C. for about 1 to about 48 hours. The alkoxide (V) may be used in an amount of about 0.1 to about 1 equivalent to 1 equivalent of the cyanopilidine derivative (IV). As the solvent, there may be used, for example, a lower alcohol corresponding to $R_6$ of the alkoxide (V), (e.g. methyl alcohol, ethyl alcohol, n-propyl alcohol, isopropyl alcohol, etc.), preferably methyl alcohol or ethyl alcohol.

After the reaction, neutralization of the solution is effected with acid, concentrated under reduced pressure and dissolved in an organic solvent. After insoluble alkali metal salt is filtered out, the filtrate is concentrated in vacuo and, if necessary, distilled to obtain the imidate derivative (VI).

A reaction between the compound (VI) and ammonium salt:

In the step, ammonium salt used is that of, for example, hydrochloric acid, hydrobromic acid, acetic acid or formic acid.

The reaction is usually carried out in the presence of a solvent at about 30° C. to about 100° C. for about 0.5 to about 5 hours. The ammonium salt may be used in amounts of about 1 to about 1.1 equivalents to 1 equivalent of the imidate derivative (VI). As the solvent, there may be used, for instance, a lower alcohol, preferably a solution of ethanol or water.

After the reaction, the reaction mixture may be concentrated in vacuo and, if necessary recrystallized to obtain such salt as hydrochloride, hydrobromide, acetate or formate of picoline amidine derivative of the formula (II).

Imidate derivature of the formula (III) is able to obtain by a method described in "Organic Functional Group Preparations Vol. III, Chapter 8, Academic Press, New York, 1971".

The pyridinyl-s-triazine derivatives of this invention may be used as an active ingredient of a fungicide, and it is usually mixed with a solid carrier, a liquid carrier, a surface active agent, and other adjuvants and formulated into emulsion, wettable powder, suspension, granule, dust or liquid.

These formulations may contain the pyridinyl-s-triazine derivative in a concentration of about 0.1 to 99% by weight, preferably about 0.2 to 95% by weight.

Examples of solid carriers include kaolin clay, attapulgite clay, bentonite, Japanese acid clay, pyrophyllite, talc, diatomaceous earth, calcite, corncob powder, walnut shell powder, urea, ammonium sulfate and synthetic hydrated silica, which are in the form of finely divided powder or granule, etc. Examples of liquid carrier include aromatic hydrocarbons, e.g., xylene and methylnaphthalene; alcohols, e.g., isopropanol, ethylene glycol, and cellosolve; ketones, e.g., acetone, cyclohexanone and isophorone; vegetable oils, e.g., soybean oil and cottonseed oil; dimethylsulfoxide, acetonitrile, water, etc.

Examples of surface active agents for emulsification, dispersion, and wetting include anionic surface active agents such as alkyl sulfate salt, alkyl or aryl sulfonate, dialkylsulfosuccinate, polyoxyethylene alkylarylether phosphate salt, and naphthalene sulfonic acid-formalin condensate; and nonionic surface active agents such as polyoxyethylene alkyl ether, polyoxyethylene-polyoxypropylene block copolymer, sorbitan-fatty acid ester, polyoxyethylene-sorbitan fatty acid ester, etc. Examples of adjuvants include ligninsulfonate, alginate, polyvinyl alcohol, gum arabic, CMC (carboxymethylcellulose), PAP (isopropyl acidphosphate), etc.

These formulations are used as such or after dilution with water for foliage application or soil treatment or soil incorporation. They may also be used in combination with other fungicide, an insecticide, acaricide, nematicide, herbicide, plant growth regulator, fertilizer or soil conditioner.

In the case where the present compound is used as an active ingredient of a fungicide, the dosage varies depending on the weather conditions, formulation, application time, application method, application place, object diseases and object crops. The dosage is usually 0.2 to 200 g, preferably 1 to 100 g for an area of 1 are. In the case of emulsion, wettable powder, suspension or liquid formulation which is diluted with water prior to application, the concentration should be 0.005 to 0.5%, preferably 0.01 to 0.2% by weight. Granules and dusts are used as such without dilution.

The present invention is explained in further detail referring to synthesis examples, formulation examples and efficiency tests.

Synthesis examples of the present compound

EXAMPLE 1

To 6-n-butyl-5-methyl-2-picoline amidine hydrochloride (1 g), was added ethyl acetimidate (1.15 g), and heated at 60° C. for 30 minutes. To the mixture, were added water (30 ml) and chloroform (30 ml), followed by extraction.

The organic layer was washed with water (30 ml) and dried over anhydrous magnesium sulfate and concentrated under reduced pressure.

The residue was subjected to silica gel column chromatography (eluent; hexane: ethylacetate=1:2 (V/V)) to obtain 2-(6-n-butyl-5-methyl-2-pyridinyl)-4,6-dimethyl-s-triazine (0.9 g).

m.p. 73.5° C.
PMR (CDCl$_3$), δppm:
2.40 (s, 3H, —CH$_3$)
2.74 (s, 6H, —CH$_3$×2)
7.51 (d, 1H, Pyridine-H$^4$, J=8.4 Hz)
8.20 (d, 1H, Pyridine-H$^3$, J=8.4 Hz)

EXAMPLE 2

To 6-o-tolyl-2-picoline amidine hydrochloride (1 g), was added ethyl acetimidate (1.05 g), and heated at 60° C. for 30 minutes.

To the mixture, were added water (30 ml) and chloroform (30 ml), followed by extraction.

The organic layer was washed with water (30 ml) and dried over anhydrous magnesium sulfate and concentrated under reduced pressure.

The residue was washed with hexane to obtain 2,4-dimethyl-(6-o-tolyl-2-pyridinyl)-s-triazine (0.85 g).

m.p. 86.8° C.
PMR (CDCl$_3$), δppm:
2.45 (s, 3H, —CH$_3$)
2.73 (s, 6H, —CH$_3$=2)
7.90 (t, 1H, Pyridine-H$^4$, J=7.8 Hz)
8.50 (d, 1H, Pyridine-H$^3$, J=7.8 Hz)

Some of compounds of this invention which can be prepared according to the similar procedure to the above are listed in Table 1.

TABLE 1

Pyridinyl-s-triazine derivatives or salts thereof.

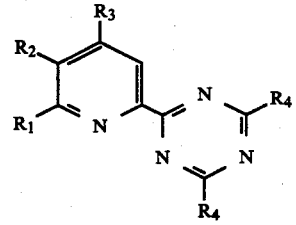

| Compound number | R$_1$ | R$_2$ | R$_3$ | R$_4$ | Physical constant |
|---|---|---|---|---|---|
| (1) | CH$_3$ | H | H | C$_2$H$_5$ | n$_D^{27.5}$ 1.5540 |
| (2) | CH$_3$ | H | H | n-C$_3$H$_7$ | n$_D^{21}$ 1.5418 |
| (3) | CH$_3$ | H | CH$_3$ | C$_2$H$_5$ | n$_D^{24}$ 1.5414 |
| (4) | C$_2$H$_5$ | H | H | C$_2$H$_5$ | n$_D^{27.5}$ 1.5412 |
| (5) | n-C$_3$H$_7$ | H | H | CH$_3$ | m.p. 58.8° C. |
| (6) | n-C$_3$H$_7$ | H | H | C$_2$H$_5$ | n$_D^{27.5}$ 1.5366 |
| (7) | n-C$_4$H$_9$ | H | H | CH$_3$ | n$_D^{21}$ 1.5553 |
| (8) | n-C$_4$H$_9$ | CH$_3$ | H | CH$_3$ | m.p. 73.5° C. |
| (9) | n-C$_5$H$_{11}$ | H | H | CH$_3$ | n$_D^{21}$ 1.5459 |
| (10) | n-C$_7$H$_{15}$ | H | H | CH$_3$ | n$_D^{21}$ 1.5390 |
| (11) | ‒(CH$_2$)$_4$‒ | | H | CH$_3$ | m.p. 111.2° C. |

TABLE 1-continued

Pyridinyl-s-triazine derivatives or salts thereof.

| Compound number | R$_1$ | R$_2$ | R$_3$ | R$_4$ | Physical constant |
|---|---|---|---|---|---|
| (12) | phenyl | H | H | CH$_3$ | n$_D^{25}$ 1.6052 |
| (13) | phenyl | H | H | C$_2$H$_5$ | m.p. 45.8° C. |
| (14) | phenyl | CH$_3$ | H | CH$_3$ | m.p. 110.8° C. |
| (15) | phenyl | CH$_3$ | H | C$_2$H$_5$ | m.p. 77.0° C. |
| (16) | o-tolyl | H | H | CH$_3$ | m.p. 86.8° C. |
| (17) | o-tolyl | CH$_3$ | H | C$_2$H$_5$ | m.p. 85.3° C. |
| (18) | o-tolyl | H | CH$_3$ | C$_2$H$_5$ | m.p. 65.5° C. |
| (19) | p-tolyl | H | H | CH$_3$ | m.p. 115.3° C. |
| (20) | p-tolyl | CH$_3$ | H | CH$_3$ | m.p. 150.0° C. |
| (21) | 3,4-dimethylphenyl | H | H | CH$_3$ | m.p. 119.3° C. |

TABLE 1-continued

Pyridinyl-s-triazine derivatives or salts thereof.

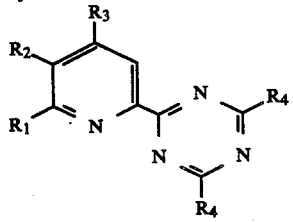

| Compound number | R₁ | R₂ | R₃ | R₄ | Physical constant |
|---|---|---|---|---|---|
| (22) | 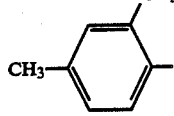 | H | H | C₂H₅ | m.p. 34.2° C. |
| (23) | 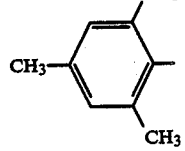 | H | H | C₂H₅ | $n_D^{24}$ 1.5622 |
| (24) | 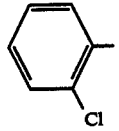 | H | H | CH₃ | m.p. 127.9° C. |
| (25) | 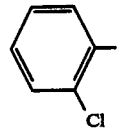 | CH₃ | H | CH₃ | m.p. 143.2° C. |
| (26) | 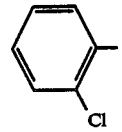 | H | CH₃ | CH₃ | m.p. 114.0° C. |
| (27) | 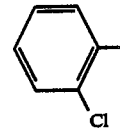 | H | CH₃ | C₂H₅ | m.p. 73.9° C. |
| (28) | 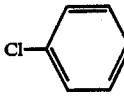 | H | H | C₂H₅ | m.p. 95.0° C. |
| (29) | 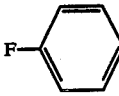 | H | H | CH₃ | m.p. 123.1° C. |
| (30) | 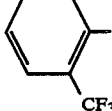 | H | H | CH₃ | m.p. 134.8° C. |

TABLE 1-continued

Pyridinyl-s-triazine derivatives or salts thereof.

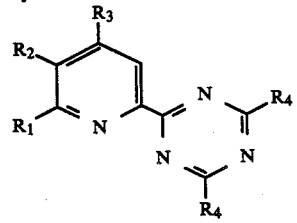

| Compound number | R₁ | R₂ | R₃ | R₄ | Physical constant |
|---|---|---|---|---|---|
| (31) | 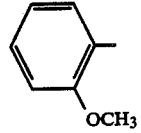 | H | H | CH₃ | m.p. 101.0° C. |
| (32) | 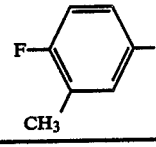 | H | H | CH₃ | m.p. 118.4° C. |
| (33) | 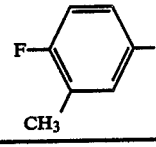 | H | H | CH₃ | m.p. 92.6° C. |

The following reference examples show the preparation of the salt of picoline amidine derivatives (II).

Reference example 1

2-Cyano-6-n-propylpyridine (10 g) was dissolved in a solution of sodium methoxide in methanol prepared from methanol (100 ml) and metallic sodium (0.32 g). After standing overnight, acetic acid (0.82 g) was added thereto, followed by concentration under reduced pressure. The resulting residue was dissolved in ether (200 ml) and insoluble materials were filtered out. The filtrate was concentrated under reduced pressure to obtain methyl 2-picoline-imidate (11.5 g, yield: 94%).

To the imidate obtained above was added a solution of ammonium chloride (3.45 g) in water (20 ml) and ethanol (80 ml) and the mixture was heated under refluxing for one hour. After being left to stand to cool, the reaction mixture was concentrated under reduced pressure. The crystalline residue obtained was washed with acetone to obtain 6-n-propyl-2-picoline amidine hydrochloride (12.2 g).

m.p. 173.0° C.

Reference example 2

2-Cyano-6-phenylpyridine (20 g) was dissolved in a solution of sodium methoxide in methanol prepared from methanol (200 ml) and metallic sodium (0.77 g). After the solution was left to stand overnight, acetic acid (2.0 g) was added thereto, followed by concentration under reduced pressure. The resulting residue was dissolved in ether (200 ml) and insoluble materials were filtered out. The filtrate was concentrated under reduced pressure to obtain methyl 2-picoline imidate.

To the imidate obtained above was added a solution of ammonium chloride (5.94 g) in water (30 ml) and ethanol (120 ml), and the mixture was heated under refluxing for one hour. After being left to stand to cool, the reaction mixture was concentrated under reduced pressure. The crystalline residue obtained was washed with acetone to obtain 6-phenyl-2-picoline amidine hydrochloride (22 g).

m.p. 166.5° C.

Some of the salt of picoline amidine derivatives of the formula (II) which are able to prepare according to the similar procedure to the above as listed in Table 2.

TABLE 2

The salt of picoline amidine derivatives

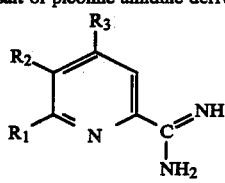

| $R_1$ | $R_2$ | $R_3$ | Physical constant |
|---|---|---|---|
| $CH_3$ | H | H | m.p. 188.0° C. (HCl-salt) |
| $CH_3$ | H | $CH_3$ | m.p. 273.0° C. (HCl-salt) |
| $C_2H_5$ | H | H | m.p. 171.8° C. (HCl-salt) |
| $n\text{-}C_3H_7$ | H | H | m.p. 173.0° C. (HCl-salt) |
| $n\text{-}C_4H_9$ | H | H | m.p. 157.0° C. (HCl-salt) |
| $n\text{-}C_4H_9$ | $CH_3$ | H | m.p. 217.4° C. (HCl-salt) |
| $n\text{-}C_5H_{11}$ | H | H | m.p. 187.2° C. (HCl-salt) |
| $n\text{-}C_7H_{15}$ | H | H | m.p. 126.2° C. (HCl-salt) |
| $-(CH_2)_4-$ | | H | m.p. 274.2° C. (HCl-salt) |
| phenyl | H | H | m.p. 166.5° C. (HCl-salt) |
| phenyl | $CH_3$ | H | m.p. 259.0° C. (HCl-salt) |
| 2-CH₃-phenyl | H | H | m.p. 209.5° C. (HCl-salt) |
| 2-CH₃-phenyl | $CH_3$ | H | m.p. 271.0° C. (HCl-salt) |
| 2-CH₃-phenyl | H | $CH_3$ | m.p. 248.0° C. (HCl-salt) |
| 4-CH₃-phenyl | H | H | m.p. 224.0° C. (HCl-salt) |

TABLE 2-continued

The salt of picoline amidine derivatives

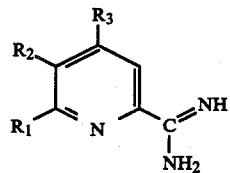

| $R_1$ | $R_2$ | $R_3$ | Physical constant |
|---|---|---|---|
| 4-CH₃-phenyl | $CH_3$ | H | m.p. 276.5° C. (HCl-salt) |
| 2,4-di-CH₃-phenyl | $CH_3$ | H | m.p. 254.0° C. (HCl-salt) |
| 2,4,5-tri-CH₃-phenyl | $CH_3$ | H | m.p. 246.5° C. (HCl-salt) |
| 2-Cl-phenyl | H | H | m.p. 246.1° C. (HCl-salt) |
| 2-Cl-phenyl | $CH_3$ | H | m.p. 266.5° C. (HCl-salt) |
| 2-Cl-phenyl | H | $CH_3$ | m.p. 237.0° C. (HCl-salt) |
| 4-Cl-phenyl | H | H | m.p. 266.6° C. (HCl-salt) |
| 4-F-phenyl | H | H | m.p. 122.8° C. (HCl-salt) |
| 3-CF₃-phenyl | H | H | m.p. 290.9° C. (HCl-salt) |

TABLE 2-continued

The salt of picoline amidine derivatives

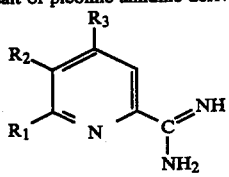

| $R_1$ | $R_2$ | $R_3$ | Physical constant |
|---|---|---|---|
| ![2-OCH3-phenyl] | H | H | m.p. 181.5° C. (HCl-salt) |
| ![4-F-2-CH3-phenyl] | H | H | m.p. 232.7° C. (HCl-salt) |
| ![4-F-3-CH3-phenyl] | H | H | m.p. 147.5° C. (HCl-salt) |

FORMULATION EXAMPLES

The present compounds used are identified by numbers shown in Table 1. Quantities are expressed by parts by weight.

Formulation Example 1

A wettable powder each was prepared by mixing and pulverizing 50 parts of each of the present compounds (1)–(33), 3 parts of calcium ligninsulfonate, 2 parts of sodium lauryl sulfate and 45 parts of synthetic hydrated silica.

Formulation Example 2

A suspension each was prepared by mixing 25 parts of each of the present compounds (1)–(33), 3 parts of polyoxethylene sorbitanmonooleate, 3 parts of CMC and 69 parts of water, followed by wet grinding to give a particle size smaller that 5 microns.

Formulation Example 3

A dust each was prepared by mixing and pulverizing 2 parts of each of the present compounds (1)–(33), 88 parts of kaolin clay and 10 parts of talc.

Formulation Example 4

An emulsifiable concentrate each was prepared by thoroughly mixing 20 parts of each of the present compounds (1)–(33), 14 parts of polyoxyethylene styrylphenyl ether, 6 parts of calcium dodecylbenzenesulfonate and 60 parts of xylene.

Formulation Example 5

A granule each was prepared by mixing and pulverizing 2 parts of each of the present compounds (1)–(33), 1 part of synthetic hydrated silica, 2 parts of calcium ligninsulfonate, 30 parts of bentonite and 65 parts of kaolin clay, followed by kneading with water, granulation and drying.

The following test examples demonstrate the effectiveness of the present compound used as an active ingredient of plant disease protectants. The present compounds used in the test examples are identified by the compound numbers shown in Table 1, and the compounds used for control are identified by the compound symbols shown in Table 3.

TABLE 3

| Compound symbol | Compound | Remarks |
|---|---|---|
| A | isoC$_3$H$_7$O–P(=O)(OisoC$_3$H$_7$)–SCH$_2$–phenyl | Commercial fungicide "IBP" |
| B | benzimidazole-2-NHCOCH$_3$ | Commercial fungicide "MBC" |
| C | tetrachloroisophthalonitrile | Commercial fungicide "TPN" |
| D | cyclohexene-dicarboximide-N-S-CCl$_2$-CHCl$_2$ | Commercial fungicide "Captafol" |
| E | pyridine-pyrimidine structure | J. Org. Chem. 27, 3608–3613 (1962) |

The controlling effect was evaluated by visually observing the degree of fungus colony and infected area of on the leaves and stems of the test plants. The results of evaluation were expressed in terms of six ratings as follows:

"5" Not observed at all.
"4" Observed on about 10% of the leaves and stems.
"3" Observed on about 30% of the leaves and stems.
"2" Observed on about 50% of the leaves and stems.
"1" Observed on about 70% of the leaves and stems.
"0" Same as control.

TEST EXAMPLE 1

Test for preventive controlling effect on blast (*Pyricularia oryzae*) of rice

Rice seeds (var.: Kinki No. 33) were sown in the sandy loam filled in a plastic pot. After raising for 20 days in a greenhouse, the seedlings were subjected to foliage application with a spray liquid of the wettable powder prepared according to Formulation Example 1 which was diluted with water to the given concentrations. After application, the seedlings were air-dried and then inoculated with spores of *Pyricularia oryzae* by spraying a suspension of spores. The inoculated seedlings were grown in a dark damp place at 28° C. for 4 days, and the controlling effect was examined. The results are shown in Table 4.

TABLE 4

| Compound No. | Concentration of active ingredient (ppm) | Control effect |
|---|---|---|
| Present compound | | |
| (1) | 200 | 5 |
| (2) | 200 | 5 |
| (3) | 200 | 5 |
| (4) | 200 | 5 |
| (5) | 200 | 5 |
| (6) | 200 | 5 |
| (7) | 200 | 5 |
| (8) | 200 | 5 |
| (9) | 200 | 5 |
| (10) | 200 | 5 |
| (11) | 200 | 5 |
| (12) | 200 | 5 |
| (13) | 200 | 5 |
| (14) | 200 | 5 |
| (15) | 200 | 5 |
| (16) | 200 | 5 |
| (17) | 200 | 5 |
| (18) | 200 | 5 |
| (19) | 200 | 5 |
| (20) | 200 | 5 |
| (21) | 200 | 5 |
| (22) | 200 | 5 |
| (23) | 200 | 5 |
| (24) | 200 | 5 |
| (25) | 200 | 5 |
| (26) | 200 | 5 |
| (27) | 200 | 5 |
| (28) | 200 | 5 |
| (29) | 200 | 5 |
| (30) | 200 | 5 |
| (31) | 200 | 5 |
| (32) | 200 | 5 |
| (33) | 200 | 5 |
| A | 200 | 4 |
| E | 400 | 0 |

Test Example 2

Test for curative controlling effect on blast (*Pyricularia oryzae*) of rice

Rice seeds (var.: Kinki No. 33) were sown in the sandy loam filled in a plastic pot. After raising for 20 days in a greenhouse, the seedlings were inoculated with spores of *Pyricularie oryzae* by spraying a suspension of spores. The inoculated seedlings were grown in a dark damp place at 28° C. for 16 hours. The seedlings were subjected to foliage application with a spray liquid of the emulsion prepared according to Formulation Example 4 which was diluted with water to the given concentrations. After application, the seedlings were grown in a dark damp place at 28° C. for 3 days, and the controlling effect was examined. The results are shown in Table 5.

TABLE 5

| Compound No. | Concentration of ingredient (ppm) | Control effect |
|---|---|---|
| present compound | | |
| (1) | 200 | 5 |
| (2) | 200 | 5 |
| (3) | 200 | 5 |
| (4) | 200 | 5 |
| (5) | 200 | 5 |

TABLE 5-continued

| Compound No. | Concentration of ingredient (ppm) | Control effect |
|---|---|---|
| (6) | 200 | 5 |
| (7) | 200 | 5 |
| (8) | 200 | 5 |
| (9) | 200 | 5 |
| (10) | 200 | 5 |
| (11) | 200 | 5 |
| (12) | 200 | 5 |
| (13) | 200 | 5 |
| (14) | 200 | 5 |
| (15) | 200 | 5 |
| (16) | 200 | 5 |
| (17) | 200 | 5 |
| (18) | 200 | 5 |
| (19) | 200 | 5 |
| (20) | 200 | 5 |
| (21) | 200 | 5 |
| (22) | 200 | 5 |
| (23) | 200 | 5 |
| (24) | 200 | 5 |
| (25) | 200 | 5 |
| (26) | 200 | 5 |
| (27) | 200 | 5 |
| (28) | 200 | 5 |
| (29) | 200 | 5 |
| (30) | 200 | 5 |
| (31) | 200 | 5 |
| (32) | 200 | 5 |
| (33) | 200 | 5 |
| A | 200 | 4 |
| E | 400 | 0 |

Test Example 3

Test for preventive controlling effect on sheath blight (*Rhizoctonia solani*) of rice Rice seeds (var.: Kinki No. 33) were sown in the sandy loam filled in a plastic pot. After raising for 28 days in a greenhouse, the seedlings were subjected to foliage application with a spray liquid of the suspension prepared according to Formulation Example 2 which was diluted with water to the given concentrations. After application, the seedlings were air-dried and then inoculated with mycelia of *Rhizoctonia solani* by spraying an agar suspension containing the fungi. The inoculated seedlings were grown in a dark damp place at 28° C. for 4 days, and the controlling effect was examined. The results are shown in Table 6.

TABLE 6

| Compound No. | Concentration of active ingredient (ppm) | Control effect |
|---|---|---|
| present compound | | |
| (1) | 400 | 5 |
| (5) | 400 | 5 |
| (6) | 400 | 5 |
| (8) | 400 | 5 |
| (10) | 400 | 5 |
| (14) | 400 | 5 |
| (15) | 400 | 5 |
| (16) | 400 | 5 |
| (17) | 400 | 5 |
| (21) | 400 | 5 |
| (22) | 400 | 5 |
| (24) | 400 | 5 |
| (25) | 400 | 5 |
| (26) | 400 | 5 |
| (27) | 400 | 5 |
| E | 400 | 0 |

Test Example 4

Test for curative controlling effect on powdery mildew (*Erysiphe graminis* f. sp. *tritici*) of wheat Wheat seeds (var.: Norin No. 78) were sown in the sandy loam filled in a plastic pot. After raising for 10 days in a greenhouse, the seedlings were inoculated with spores of *Erysiphe graminis* f. sp. *tritici*. The inoculated seedlings were grown at 23° C. for 3 days. The seedlings were subjected to foliage application with a spray liquid of the suspension prepared according to Formulation Example 2 which was diluted with water to the given concentrations. After application, the seedlings were grown in a greenhouse at 23° C. for 7 days, and the controlling effect was examined. The results are shown in Table 7.

TABLE 7

| Compound No. | Concentration of active ingredient (ppm) | Control effect |
|---|---|---|
| present compound | | |
| (15) | 400 | 5 |
| (18) | 400 | 5 |
| (22) | 400 | 5 |
| E | 400 | 0 |

Test Example 5

Test for preventive controlling effect on brown leaf spot (*Cercospora arachidicola*) of peanut Peanut seeds (var.: Chiba hanritsu) were sown in the sandy loam filled in a plastic pot. After raising for 14 days in a greenhouse, the seedlings were subjected to foliage application with a spray liquid of the wettable powder prepared according to Formulation Example 1 which was diluted with water to the given concentrations. After application, the seedlings were air-dried and inoculated with spores of *Cercospora arachidicola* by spraying a suspension of spores. The inoculated seedlings were placed in a damp place at 23° C. for 7 days and then grown in a greenhouse for 7 days. The controlling effect was examined. The results are shown in Table 8.

TABLE 8

| Compound No. | Concentration of active ingredient (ppm) | Control effect |
|---|---|---|
| present compound | | |
| (4) | 400 | 5 |
| (15) | 400 | 5 |
| (17) | 400 | 5 |
| (21) | 400 | 5 |
| (22) | 400 | 5 |
| (30) | 400 | 5 |
| E | 400 | 0 |

Test Example 6

Test for preventive controlling effect on anthracnose (*Colletotrichum lagenarium*) of cucumber Cucumber seeds (var.: Sagami hanjiro) were sown in the sandy loam filled in a plastic pot. After raising for 14 days in a greenhouse, the seedlings were subjected to foliage application with a spray liquid of the emulsion prepared according to Formulation Example 4 which was diluted with water to the given concentrations. After application, the seedlings were air-dried and then inoculated with spores of *Colletotrichum lagenarium* by spraying a suspension containing the spores. The inoculated seedlings were left to stand in a dark damp place at 23° C. for one day and then were grown under lightening for 4 days. The controlling effect was examined. The results are shown in Table 9.

TABLE 9

| Compound No. | Concentration of active ingredient (ppm) | Control effect |
|---|---|---|
| present compound | | |
| (6) | 400 | 5 |
| (8) | 400 | 5 |
| (10) | 400 | 5 |
| (13) | 400 | 5 |
| (14) | 400 | 5 |
| (15) | 400 | 5 |
| (16) | 400 | 5 |
| (17) | 400 | 5 |
| (18) | 400 | 5 |
| (19) | 400 | 5 |
| (21) | 400 | 5 |
| (22) | 400 | 5 |
| (27) | 400 | 5 |
| C | 400 | 4 |
| E | 400 | 0 |

Test Example 7

Test for preventive controlling effect on scab (*Venturia inaequalis*) of apple

Apple seeds (var.: Kogyoku) were sown in the sandy loam filled in a plastic pot. After raising for 20 days in a greenhouse, the seedlings, with the fourth to fifth foliage leaves open, were subjected to foliage application with a spray liquid of the wettable powder prepared according to Formulation Example 1 which was diluted with water to the given concentrations. After application, the seedlings were air-dried and then inoculated with spores of *Venturia inaequalis* by spraying a suspension containing the spores. The inoculated seedlings were grown in a dark damp place at 15° C. for 4 days, and then grown under lightening for 15 days. The controlling effect was examined. The results are shown in Table 10.

TABLE 10

| Compound No. | Concentration of active ingredient (ppm) | Control effect |
|---|---|---|
| present compound | | |
| (3) | 400 | 5 |
| (4) | 400 | 5 |
| (6) | 400 | 5 |
| (8) | 400 | 5 |
| (10) | 400 | 5 |
| (11) | 400 | 5 |
| (13) | 400 | 5 |
| (14) | 400 | 5 |
| (15) | 400 | 5 |
| (16) | 400 | 5 |
| (18) | 400 | 5 |
| (19) | 400 | 5 |
| (21) | 400 | 5 |
| (22) | 400 | 5 |
| (24) | 400 | 5 |
| (25) | 400 | 5 |
| (29) | 400 | 5 |
| E | 400 | 0 |

Test Example 8

Test for preventive controlling effect on gray mold (*Botrytis cinerea*) of cucumber Cucumber seeds (var.: *Sagami hanjiro*) were sown in the sandy loam filled in a plastic pot. After raising for 14 days in a greenhouse, the seedlings were subjected to foliage application with a spray liquid of the emulsion prepared according to Formulation Example 4 which was diluted with water to the given concentrations. After application, the seedlings were air-dried and then inoculated with mycelia of *Botrytis cinerea* which is resistant to benzimidazole thiophanate fungicide. The inoculated seedlings were grown in a dark damp place at 15° C. for 3 days, and the controlling effect was examined. The results are shown in Table 11.

TABLE 11

| Compound No. | Concentration of active ingredient (ppm) | Control effect |
|---|---|---|
| present compound | | |
| (16) | 400 | 5 |
| (19) | 400 | 5 |
| (21) | 400 | 5 |
| (24) | 400 | 5 |
| (25) | 400 | 5 |
| (26) | 400 | 5 |
| (27) | 400 | 5 |
| B | 400 | 0 |
| E | 400 | 0 |

Test Example 9

Test for curative controlling effect on speckled leaf blotch (*Septoria tritici*) of wheat Wheat seeds (var.: Norin No. 73) were sown in the sandy loam filled in a plastic pot. After raising for 8 days in a greenhouse, the seedlings were inoculated with spores of *Septoria tritici* by spraying a suspension of spores. The inoculated seedlings were grown in a dark damp place at 15° C. for 3 days, and then grown for 4 days under lightening. The seedlings were subjected to foliage application with a spray liquid of the wettable powder prepared according to Formulation Example 1 which was diluted with water to the given concentration. After application, the seedlings were grown at 15° C. for 11 days under illumination, and the controlling effect was examined. The results are shown in Table 12.

TABLE 12

| Compound No. | Concentration of active ingredient (ppm) | Control effect |
|---|---|---|
| present compound | | |
| (1) | 400 | 5 |
| (5) | 400 | 5 |
| (6) | 400 | 5 |
| (8) | 400 | 5 |
| (9) | 400 | 5 |
| (12) | 400 | 5 |
| (13) | 400 | 5 |
| (14) | 400 | 5 |
| (15) | 400 | 5 |
| (16) | 400 | 5 |
| (17) | 400 | 5 |
| (18) | 400 | 5 |
| (19) | 400 | 5 |
| (21) | 400 | 5 |
| (22) | 400 | 5 |
| (24) | 400 | 5 |
| (25) | 400 | 5 |
| (26) | 400 | 5 |
| (27) | 400 | 5 |
| (28) | 400 | 5 |
| (29) | 400 | 5 |
| (30) | 400 | 5 |

TABLE 12-continued

| Compound No. | Concentration of active ingredient (ppm) | Control effect |
|---|---|---|
| (32) | 400 | 5 |
| (33) | 400 | 5 |
| D | 400 | 0 |
| E | 400 | 0 |

Test Example 10

Test for preventive controlling effect on eyespot (*Pseudocercosporella herpotrichoides*) of wheat Wheat seeds (var.: Norin No. 73) were sown in the sandy loam filled in a plastic pot. After raising for 10 days in a greenhouse, the seedlings were subjected to foliage application with a spray liquid of the emulsion prepared according to Formulation Example 4 which was diluted with water to the given concentrations. After application, the seedlings were air-dried and then inoculated with MBC-resistant spores of *Pseudocercosporella herpotrichoides* by spraying a suspension containing the spores. The inoculated seedlings were grown in a dark damp place at 15° C. for 4 days, further incubated for 4 days under illumination, and the controlling effect was examined. The results are shown in Table 13.

TABLE 13

| Compound No. | Concentration of active ingredient (ppm) | Control effect |
|---|---|---|
| present compound | | |
| (5) | 400 | 5 |
| (8) | 400 | 5 |
| (13) | 400 | 5 |
| (14) | 400 | 5 |
| (15) | 400 | 5 |
| (16) | 400 | 5 |
| (17) | 400 | 5 |
| (18) | 400 | 5 |
| (19) | 400 | 5 |
| (21) | 400 | 5 |
| (22) | 400 | 5 |
| (24) | 400 | 5 |
| (25) | 400 | 5 |
| (26) | 400 | 5 |
| (27) | 400 | 5 |
| (28) | 400 | 5 |
| (29) | 400 | 5 |
| (30) | 400 | 5 |
| B | 400 | 0 |
| E | 400 | 0 |

We claim:

1. A pyridinyl-s-triazine derivative of the formula:

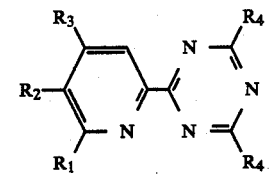

wherein $R_1$ is a $C_1$–$C_7$ alkyl group; or a phenyl group optionally substituted with at least one member selected from the group consisting of halogen, $C_1$–$C_3$ alkyl, $C_1$–$C_3$ alkoxy and $C_1$–$C_3$ haloalkyl group; $R_2$ and $R_3$ which the same or different, are a hydrogen atom or a $C_1$–$C_3$ alkyl group, or $R_1$ and $R_2$ are, taken together, a polymethylene group of the formula: $-(CH_2)_n-$ in which n is 3 or 4 and $R_4$ is a $C_1$–$C_4$ alkyl group, with the proviso that when $R_1$ is methyl or ethyl group, $R_4$ is not methyl group, or its salt.

2. Pyridinyl-s-triazine derivative according to claim 1, wherein $R_1$ is a $C_3$–$C_5$ alkyl group; or a phenyl group optionally substituted with at least one member selected from the group consisting of halogen, methyl, ethyl, methoxy, ethoxy and trifluoromethyl group; $R_2$ and $R_3$ which, the same or different, are a hydrogen atom or a methyl group and $R_4$ is a $C_1$–$C_3$ alkyl group, or its salt.

3. Pyridinyl-s-triazine derivative according to claim 1, wherein $R_1$ is a $C_3$–$C_5$ alkyl group; $R_2$ and $R_3$ which, the same or different, are a hydrogen atom or methyl group and $R_4$ is a $C_1$–$C_3$ alkyl group, or its salt.

4. Pyridinyl-s-triazine derivative according to claim 1, wherein $R_1$ is a phenyl group optionally substituted with at least one member selected from the group consisting of halogen, methyl and trifluoromethyl group; $R_2$ and $R_3$ which, the same or different, are a hydrogen atom or methyl group and $R_4$ is a $C_1$–$C_3$ alkyl group, or its salt.

5. Pyridinyl-s-triazine derivative according to claim 1, wherein the derivative is at least one member selected from the group consisting of
2,4-Di-n-propyl-6-(6-methyl-2-pyridinyl)-s-triazine,
2,4-Diethyl-6-(6-propyl-2-pyridinyl)-s-triazine,
2-(6-n-Butyl-5-methyl-2-pyridinyl)-4,6-dimethyl-s-triazine,
2,4-Dimethyl-6-(6-phenyl-2-pyridinyl)-s-triazine,
2,4-Diethyl-6-(6-phenyl-2-pyridinyl)-s-triazine,
2-(6-o-Chlorophenyl-2-pyridinyl)-4,6-dimethyl-s-triazine,
2,4-Dimethyl-6-(5-methyl-6-phenyl-2-pyridinyl)-s-triazine,
2,4-Dimethyl-6-(6-$\alpha,\alpha,\alpha$,-trifluoro-o-tolyl-2-pyridinyl)-s-triazine and their salts.

6. A fungicidal composition which comprises as an active ingredient a fungicidally effective amount of a pyridinyl-s-triazine derivative of the formula:

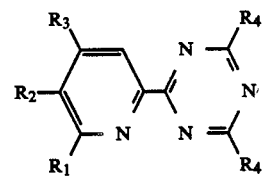

wherein $R_1$ is a $C_1$–$C_7$ alkyl group; or a phenyl group optionally substituted with at least one member selected from the group consisting of halogen $C_1$–$C_3$ alkyl, $C_1$–$C_3$ alkoxy and $C_1$–$C_3$ haloalkyl; $R_2$ and $R_3$ which, the same or different, are a hydrogen atom or a $C_1$–$C_3$ alkyl group, or $R_1$ and $R_2$ are, taken together, a polymethylene group of the formula: $+CH_2)_n$ in which n is 3 or 4 and $R_4$ is a $C_1$–$C_4$ alkyl group, with the proviso that when $R_1$ is methyl or ethyl group, $R_4$ is not methyl group, or its salt, with an inert carrier.

7. A method for controlling plant pathogenic fungi which comprises applying a fungicidally effective amount of the pyridinyl-s-triazine derivative of the formula:

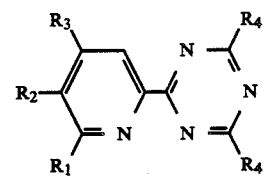

wherein $R_1$, $R_2$, $R_3$ and $R_4$ are as defined as claim 1, to plant pathogenic fungi.

* * * * *